United States Patent
Burk

Patent Number: 6,124,344
Date of Patent: *Sep. 26, 2000

[54] CYCLOPENTANE HEPTAN(ENE)OIC ACID, 2-HETEROARYLALKENYL DERIVATIVES AS THERAPEUTIC AGENTS

[75] Inventor: Robert M. Burk, Laguna Beach, Calif.

[73] Assignee: Allergan Sales, Inc.

[*] Notice: This patent is subject to a terminal disclaimer.

[21] Appl. No.: 08/974,067

[22] Filed: Nov. 19, 1997

Related U.S. Application Data

[60] Continuation-in-part of application No. 08/861,414, May 21, 1997, Pat. No. 5,798,378, which is a division of application No. 08/740,883, Nov. 4, 1996, Pat. No. 5,681,848, which is a division of application No. 08/445,842, Jul. 11, 1995, Pat. No. 5,587,391, which is a division of application No. 08/174,535, Dec. 28, 1993, Pat. No. 5,545,665.

[51] Int. Cl.$^7$ ..................... C07D 333/16; C07D 307/02; A61K 31/38

[52] U.S. Cl. ..................... 514/438; 514/461; 549/78; 549/474; 549/497; 549/502

[58] Field of Search ..................... 514/438, 461; 549/78, 474, 497, 502

[56] References Cited

PUBLICATIONS

CA 121:141686, 1994.
CA 123:339522, 1995.
CA 121:26934, 1994.
CA 126;74671, 1996.
CA 78:159053, 1973.
CA 90:197992, 1979.
CA 93:198357, 1980.
CA 81:3472, 1974.
CA 85:46078, 1976.
CA 86:55061, 1976.
CA 86:55065, 1976.

*Primary Examiner*—D. Margaret M. Mach
*Attorney, Agent, or Firm*—Robert J. Baran; Martin A. Voet; Carlos A. Fisher

[57] ABSTRACT

The invention relates to the use of derivatives of F-type prostaglandins as ocular hypotensives. The compounds used in accordance with the invention are represented by the following formula I:

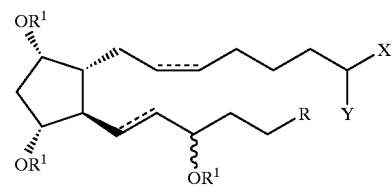

wherein wavy line attachments indicate either the alpha ($\alpha$) or beta ($\beta$) configuration; hatched segments indicate a configuration; the solid triangle is used to indicate $\beta$ configuration; dashed bonds represent a double bond, or a single bond; R is a substituted heteroaryl radical having at least two pendant substituents selected from the group consisting of $C_1$ to $C_6$ alkyl; halogen; trifluoromethyl; $COR^1$; $COCF_3$; $SO_2NR^1$; $NO_2$ and CN or at least one cyano group; $R^1$ is hydrogen or a lower alkyl radical having up to six carbon atoms, X is selected from the group consisting of —$OR^1$ and —$N(R^1)_2$; Y is =O or represents 2 hydrogen radicals and the 9, 11 or 15 lower alkyl esters thereof; provided, however, when said heteroaryl radical is a dichlorothienyl radical, the compound is not a 1-carboxylic add or amide thereof. Certain of the compounds represented by Formula I are novel and comprise another aspect of the present invention.

24 Claims, 3 Drawing Sheets

1

2a-e 3a-e 4a-e 5a-e

CYCLOPENTANE HEPTAN(ENE)OIC ACID, 2-HETEROARYLALKENYL DERIVATIVES AS THERAPEUTIC AGENTS

CROSS REFERENCE TO RELATED APPLICATIONS

The present patent application is a continuation in part of U.S. patent application Ser. No. 861,414, filed on May 21, 1997 now U.S. Pat. No. 5,798,378, which is a division of U.S. patent application Ser. No. 740,883, filed Nov. 4, 1996, now U.S. Pat. No. 5,681,848, which is a division of U.S. patent application Ser. No. 445,842, filed Jul. 11, 1995, now U.S. Pat. No. 5,587,391, which is a division of U.S. patent application Ser. No. 174,535, filed Dec. 28, 1993, now U.S. Pat. No. 5,545,665.

BACKGROUND OF THE INVENTION

1. Field of the Invention

The present invention relates to cyclopentane heptanoic acid, 2 heteroarylalkenyl derivatives which may be substituted in the 1-position with hydroxyl, alkyloxy, amino and amido groups, e.g. 1-OH cyclopentane heptanoic acid, 2 heteroarylalkenyl derivatives. These compounds are potent ocular hypotensive and are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

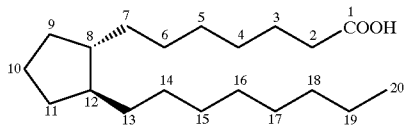

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or α [[erg. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins.* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105. 1036 (1987), and Siebold et.al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990), relates to certain 1-acyl-prostaglandins, such as 11-pivaloyl, 1-acetyl, 1-isobutyryl, 1-valeryl, and 11-isovaleryl $PGF_{2\alpha}$. Intraocular pressure reducing 15-acyl prostaglandins are disclosed in the co-pending application U.S. Ser. No. 175, 476 (filed Dec. 29, 1993). Similarly, 11,15-9,15 and 9,11- diesters of prostaglandins, for example 11,15-dipivaloyl $PGF_{2\alpha}$ are known to have ocular hypotensive activity. See the co-pending patent applications U.S. Ser. No. Nos. 385, 645 (filed Jul. 7, 1989, now U.S. Pat. No. 4,994,274), 584,370 (filed Sep. 18, 1990, now U.S. Pat. No. 5,028,624) and 585,284 (filed Sep. 18, 1990, now U.S. Pat. No. 5,034, 413). The disclosures of all of these patent applications are hereby expressly incorporated by reference in their entirety. This patent application is also related to U.S. patent application Ser. No. 08/726,921, which was filed on Oct. 7, 1996 in the name of Burk, which is a File Wrapper Continuation of U.S. patent application Ser. No. 08/443,992 which was filed on May 18, 1995 in the name of Burk, both of which patent applications are expressly incorporated by reference in their entirety.

SUMMARY OF THE INVENTION

The present invention concerns a method of treating ocular hypertension which comprises administering to a mammal having ocular hypertension a therapeutically effective amount of a compound of formula I

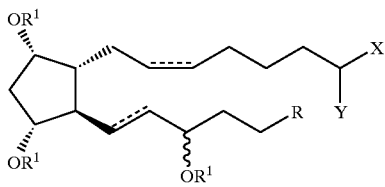

wherein the hatched segments represent a bonds, the solid triangle represents a β bond, the wavy segment represents α or β bond, dashed lines represent a double bond or a single bond, R is a substituted heteroaryl radical having at least two pendant substituents selected from the group consisting of lower alkyl, e.g. C1 to $C_6$ alkyl; halogen; trifluoromethyl; $COR^1$, $COCF_3$; $SO_2NR^1$; $NO_2$; CN or at least one cyano substitutent, i.e. CN; $R^1$ is hydrogen or a lower alkyl radical having up to six carbon atoms, X is selected from the group consisting of $-OR^1$ and $-N(R^1)_2$, Y is=O or represents 2 hydrogen radicals, and the 9, 11, or 15 lower alkyl esters thereof; provided, however, when said heteroaryl radical is a dichloro thienyl radical, said compound is not a 1-carboxylic acid or amide thereof. In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application. In particular, the substituents on the heteroaryl radical may be selected from the group consisting of lower alkyl, e.g. $C_1$ to $C_6$ alkyl; halogen, e.g. fluoro, chloro and bromo; trifluoromethyl ($CF_3$); $COR^1$, e.g. $COCH_3$; $COCF_3$; $SO_2NR^1$, e.g. $SO_2NH_2$l $NO_2$; CN; etc.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

BRIEF DESCRIPTION OF THE DRAWING FIGURES

DETAILED DESCRIPTION OF THE INVENTION

Figure 1:
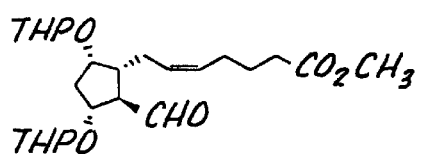
FIG. 1 is a schematic of the chemical synthesis of certain 1-carboxylic acid compounds of the invention specifically disclosed in Example 5(a)–(e) below.
Figure 1:
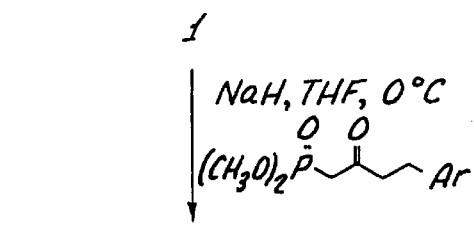
Figure 1:
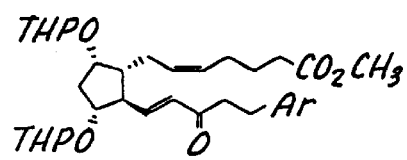
Figure 1:
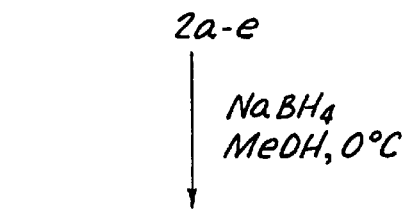
Figure 1:
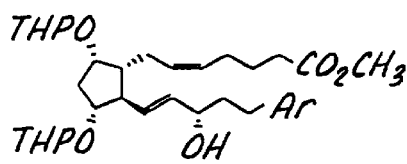
Figure 1:
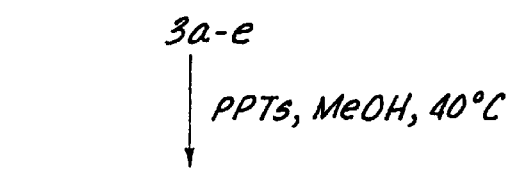
Figure 1:
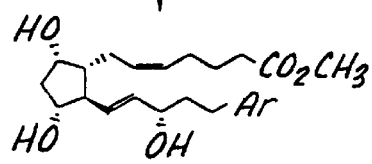
Figure 1:
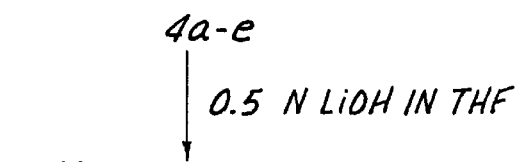
Figure 1:
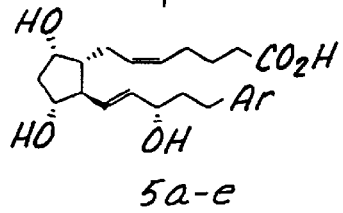

The present invention relates to the use of nonacidic cyclopentane heptan(ene)oic acid, 2-heteroaryl alkenyl derivatives as therapeutic agents, e.g. as ocular hypotensives. The compounds used in accordance with the present invention are encompassed by the following structural formula I:

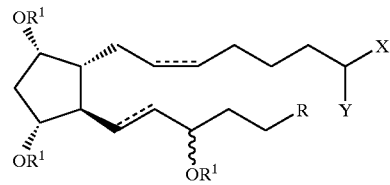

wherein the substituents and symbols are as hereinabove defined. The dotted lines on bonds between carbons 5 and 6 (C-5) and carbons 13 and 14 (C-13) indicate a single or double bond. If two solid lines are used at C-5, or C-13, it indicates a specific configuration for that double bond. Hatched lines used at position C-8, C-9 and C-11 indicate the a configuration. A triangle at position C-12 represents β orientation.

A preferred group of the compounds of the present invention includes compounds that have the following structural formula II:

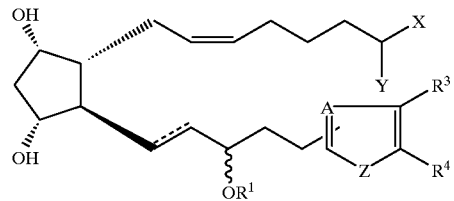

wherein Z is selected from the group consisting of O and S; A is selected from the group consisting of C or $CR^2$; $R^2$, $R^3$ and $R^4$ are selected from the group consisting of hydrogen, cyano, halogen and lower alkyl having from 1 to 6 carbon atoms. Preferably, when X is $-N(R^1)_2$, Y is =O. More preferably, at least one of $R^2$, $R^3$ or $R^4$ are independently selected from the group consisting of chloro, bromo, iodo, cyano and methyl.

In one aspect of the invention, at least one of $R^2$, $R^3$ or $R^4$ is 5 bromo, and at least one other of $R^2$, $R^3$ or $R^4$ is bromo or methyl, or $R^2$, $R^3$ and $R^4$ are chloro, or at least one other of $R^2$, $R^3$ or $R^4$ is methyl and at least one other of $R^2$, $R^3$ and $R^4$ is bromo or iodo. In another aspect of this invention, $R^2$ is cyano and $R^3$ and $R^4$ are hydrogen.

Another preferred group includes compounds having the formula III:

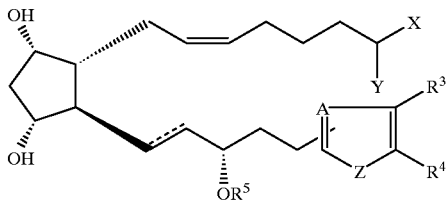

In the above formulae, the substituents and symbols are as hereinabove defined and $R^5$ is hydrogen.

The above compounds of the present invention may be prepared by methods that are known in the art or according to the working examples below. The compounds, below, are especially preferred representative of the compounds of the present invention.

7-[3α, 5α-Dihydroxy-2-(3α-hydroxy-5-(5-(2-cyano) thienyl)-1E-pentenyl)cyclopentyl]-5Z-heptenoic acid (5a)

7-[3α, 5α-Dihydroxy-2-(3α-hydroxy-5-(5-(2,3,4-trichloro) thienyl)-1E-pentenyl)cyclopentyl]-5Z-heptenoic acid (5b)

7-[3α, 5α-Dihydroxy-2-(3α-hydroxy-5-(5-(2,3-dichloro) thienyl)-1E-pentenyl)cyclopentyl]-5Z-heptenoic acid (5c)

7-[3α, 5α-Dihydroxy-2-(3α-hydroxy-5-(5-(2-iodomethyl) thienyl)-1E-pentenyl)cyclopentyl]-5Z-heptenoic acid (5d)

7-[3α, 5α-Dihydroxy-2-(3α-hydroxy-5-((3-bromo-2,5-dimethyl)thienyl)-1E-pentenyl)cyclopentyl]-5Z-heptenoic acid (5e)

7-[3α, 5α-Dihydroxy-2-(3α-hydroxy-5-(3-(2,5-dichloro) thienyl)pentyl)-cyclopentyl]-5Z-heptenoic acid (5f)

7-[3α, 5α-Dihydroxy-2-(3α-hydroxy-5-(5-(2-cyano) thienyl)-1E-pentenyl)cyclopentyl]-5Z-heptenamide (11a)

7-[3α, 5α-Dihydroxy-2-(3α-hydroxy-5-(5-(2,3,-trichloro) thienyl)-1E-pentenyl)cyclopentyl]-5Z-heptenamide (11b)

7-[3α, 5α-Dihydroxy-2-(3α-hydroxy-5-(-(5-(2,3-dichloro) thienyl)-1E -pentenyl)cyclopentyl]-5Z-heptenamide (11c)

7-[3α, 5α-Dihydroxy-2-(3α-hydroxy-5-(5-(2-iodo-4-methyl)thienyl)-1E-pentenyl)cyclopentyl]-5Z-heptenamide (11d)

7-[3α, 5α-Dihydroxy-2-(3α-hydroxy-5-(3-(2,5-dichloro) thienyl)-pentyl)cyclopentyl]-5Z-heptenamide (11f)

N-2-Hydroxyethyl 7-[3α, 5α-dihydroxy-2-(3α-hydroxy-5-(5-(3-bromo-2-methyl)thienyl)-1E-pentenyl) cyclopentyl]-5Z-heptenamide (11g)

N-Ethyl 7-[3α, 5α-dihydroxy-2-(3α-hydroxy-5-(5-(3-bromo-2-methyl)thienyl)-1E-pentenyl)cyclopentyl]-5Z-heptenamide (11h)

N-2-Hydroxyethyl 7-[3α, 5α-dihydroxy-2-(3α-hydroxy-5-(3-(2,5-dibromo)-thienyl)-1E-pentenyl)cyclopentyl]-5Z-heptenamide (11i)

N-Ethyl 7-[3α, 5α-dihydroxy-2-(3α-hydroxy-5-(3-(2,5-dibromo)-thienyl)-1E-pentenyl)cyclopentyl]-5Z-heptenamide (11j)

Isopropyl 7-[3α, 5α-Dihydroxy-2-(3α-hydroxy-5-(5-(2-cyano)thienyl)-1E-pentenyl)cyclopentyl]-5Z-heptenoate (12a)

Isopropyl 7-[3α, 5α-Dihydroxy-2-(3α-hydroxy-5-(5-(2,3,4-chloro)-thienyl)-1E-pentenyl)cyclopentyl]-5Z-heptenoate (12b)

Isopropyl 7-[3α, 5α-Dihydroxy-2-(3α-hydroxy-5-(5-(3-bromo-2-methyl)-thienyl)-1E-pentenyl)cyclopentyl]-5Z-heptenoate (12k)

Isopropyl 7-[3α, 5α-Dihydroxy-2-(3α-hydroxy-5-(3-(2,5-dibromo)-thienyl)-1E-pentenyl)cyclopentyl]-5Z-heptenoate (12ll)

A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjuster | 1–10 |
| buffer | 0.01–10 |
| pH adjuster | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 2:
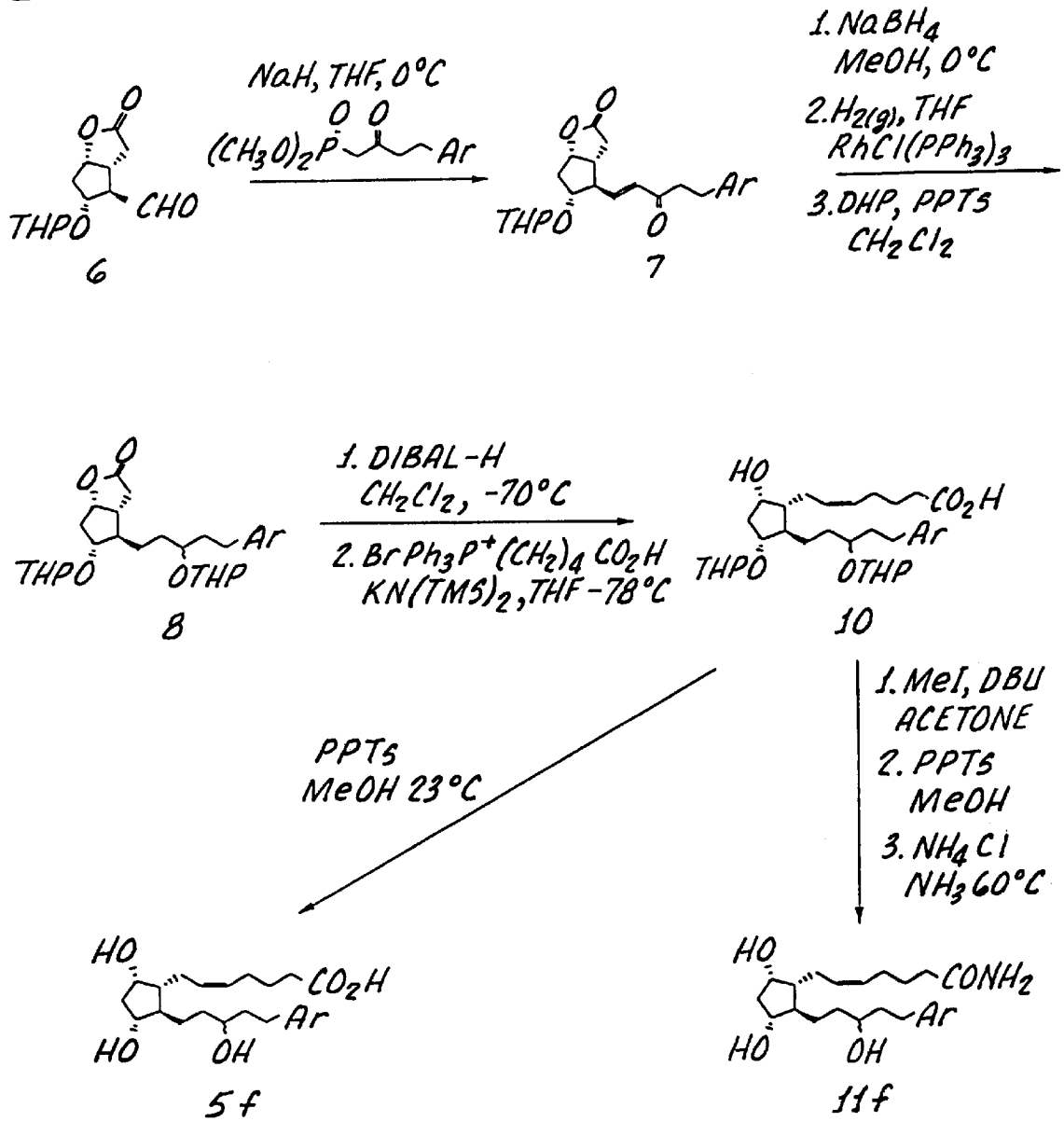
FIG. 2 is a schematic of the chemical synthesis of certain 1-carboxylic acid or 1-amido compounds of the invention specifically disclosed in Example 5(f) and 11(f), below.
Figure 3:
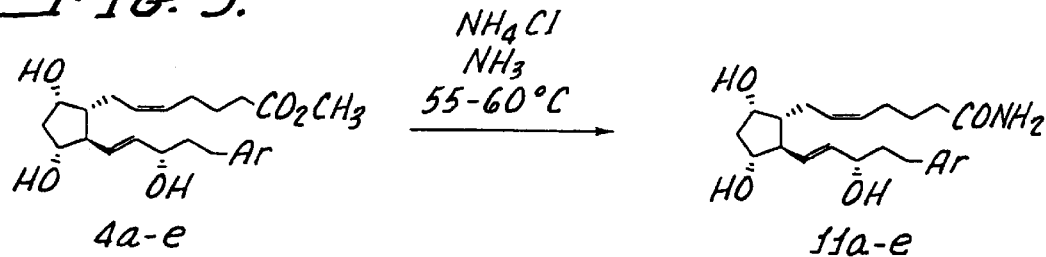
FIG. 3 is a schematic of the chemical synthesis of certain 1-amido compounds of the invention specifically disclosed in Examples 11(a)–(e), below.
Figure 4:
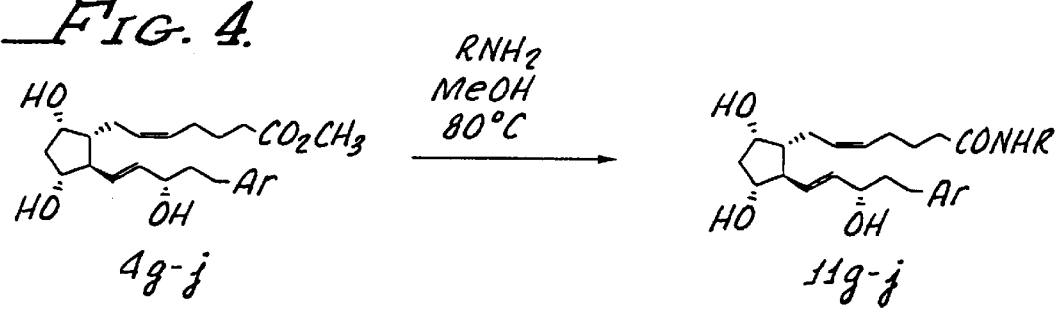
FIG. 4 is a schematic of the chemical synthesis of certain 1-amido compounds of the invention as specifically disclosed in Examples 11 (g)–(j), below.
Figure 5:
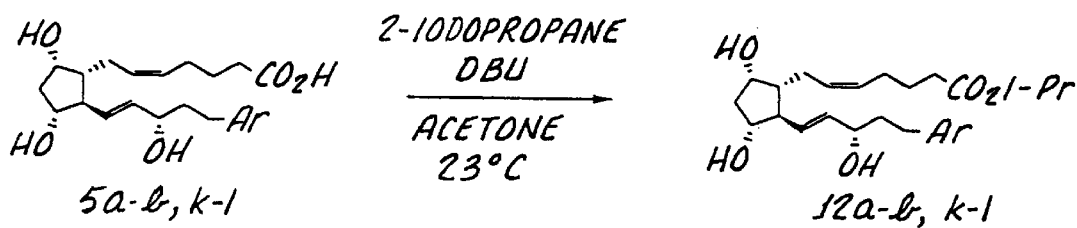
FIG. 5 is a schematic of the chemical synthesis of 1-isopropylester compounds of the invention as specifically disclosed in Examples 12 (a)–(b) and 12(k)–(l), below.

The invention is further illustrated by the following non-limiting Examples, which are summarized in the reaction schemes of FIGS. 1 through 5, wherein the compounds are identified by the same designator in both the Examples and the Figures.

EXAMPLE 1

7-[3α, 5α-Dihydroxy-2-(3α-hydroxy-5-(5-(2-cyano) thienyl)-1E-pentenyl)cyclopentyl]-5Z-heptenoic acid (5a)

Step 1: Preparation of enone (2a)

To a suspension of sodium hydride (26 mg, 1.14 mmol) in tetrahydrofuran (THF) (2.1 mL) cooled to 0° C. was added dimethyl 4-(5-(2-cyano)thienyl)-2-oxobutylphosphonate (325 mg, 1.14 mmol) in THF (2.1 mL). After 15 minutes a solution of aldehyde 1(500 mg, 1.03 mmol) in THF (3.0 mL) was added and the reaction solution was allowed to slowly warm to 23° C. over a period of 8 h. The reaction was quenched with saturated aqueous $NH_4Cl$ and extracted with ethylacetate (EtOAc). The combined organics were washed with brine, dried over $MgSO_4$, filtered and concentrated in vacuo. Purification by flash column chromatography (FCC) (silica gel, 3:1 hexane/EtOAc) provided 231 mg (37%) of enone 2a.

Step 2: Preparation of α-alcohol (3a)

Sodium tetrahydridoborate (15 mg, 0.40 mmol) was added to a solution of enone 2a (231 mg, 0.38 mmol) in MEOH (3.0 mL) at 0° C. After 1 h the solvent was removed in vacuo and the residue was stirred with 1N NaOH and EtOAc for 0.5 h. The resultant mixture was extracted twice with EtOAc. The combined organic portions were washed with brine, dried over $MgSO_4$, filtered and concentrated in vacuo. Purification of the residue by flash column chromatography (silica gel, 2:1 hexane/EtOAc) afforded 66 mg (29%) of pure α-alcohol 3a.

Step 3: Preparation of trihydroxy ester (4b/)

A solution of the α-alcohol 3b (66 mg, 0.11 mmol) and pyridinium p-toluenesulfonate (33 mg, 0.13 mmol) in MEOH (1.0 mL) was stirred at 23° C. for 12 h. The solvent was removed in vacuo. The residue was diluted with EtOAc and then washed with 1N HCl, saturated aqueous $NaHCO_3$, and brine. The organic portion was dried over $MgSO_4$, filtered and concentrated in vacuo. Purification of the residue by flash column chromatography (silica gel, 100% EtOAc) gave 28 mg (59%) of trihydroxy ester 4b.

Step 4: Saponification of trihydroxy ester (4a)

Lithium hydroxide (0.3 mL of a 0.5 N solution in $H_2O$, 0.15 mmol) was added to a solution of the trihydroxy ester 4a (28 mg, 0.081 mmol) in THF (0.6 mL) at 23° C. After 16 h the reaction mixture was acidified with 1N HCl and extracted with EtOAc. The organic portion was washed twice with brine, dried over $Na_2SO_4$, filtered and concentrated in vacuo. The residue was purified by flash column chromatography (silica gel, 9:1 $CH_2Cl_2$/MeOH) to afford 16 mg (60%) of the title compound 5a.

EXAMPLE 2

7-[3α, 5α-Dihydroxy-2-(3α-hydroxy-5-(5-(2,3,4-trichloro)thienyl)-1E-pentenyl)cyclopentyl-5Z-heptenoic acid (5b)

In accordance with the procedures described above for the synthesis of 5a, the use of dimethyl 4-(5-(2,3,4-triiodo) thienyl)-2-oxobutylphosphonate afforded 38 mg of free acid 5b.

EXAMPLE 3

7-[3α, 5α-Dihydroxy-2-(3α-hydroxy-5-(5-(2,3-dichloro)thienyl)-1E-pentenyl)cyclopentyl]-5Z-heptenoic acid (5c)

In accordance with the procedures described above for the synthesis of 5a, the use of dimethyl 4-(5-(2,3-dichloro) thienyl)-2-oxobutylphosphonate afforded 10 mg of free acid 5c.

EXAMPLE 4

7-[3α, 5α-Dihydroxy-2-(3α-hydroxy-(5-(2-iodo-4-methyl)thienyl)-1E-pentenyl)cyclopentyl]-5Z-heptenoic acid (5d)

In accordance with the procedures described above for the synthesis of 5a, the use of dimethyl 4-(5-(2-iodo-4-methyl) thienyl)-2-oxobutylphosphonate afforded 22 mg of free acid 5d.

EXAMPLE 5

7-[3α, 5α-Dihydroxy-2-(3α-hydroxy-5-(4-(3-bromo-2,5-dimethyl)thienyl)-1E-pentenyl) cyclopentyl]-5Z-heptenoic acid (5e)

In accordance with the procedures described above for the synthesis of 5a, the use of dimethyl 4-(4-(3-bromo-2,5-dimethyl)thienyl)-2-oxobutylphosphonate afforded 9 mg of free acid 5e.

EXAMPLE 6

7-[3α, 5α-Dihydroxy-2-(3α-hydroxy-5-(3-(2,5-dichloro)thienyl)pentyl)-cyclopentyl]-5Z-heptenoic acid (5f)

Step 1: Preparation of enone (7)

To a suspension of sodium hydride (370 mg, 15.4 mmol) in tetrahydrofuran (THF) (12.0 mL) cooled to 0° C. was added dimethyl 4-(3-(2,5-dichloro)thienyl)-2-oxobutylphosphonate (5.1 g, 15.4 mmol) in THF (8.0 mL). After 15 minutes a solution of aldehyde 6 (3.55 g, 14.0 mmol) in THF (5.0 mL) was added and the reaction solution was allowed to slowly warm to 23° C. over a period of 8 h. The reaction was quenched with saturated aqueous NH$_4$Cl and extracted with EtOAc. The combined organics were washed with brine, dried over MgSO$_4$, filtered and concentrated in vacuo. Purification by flash column chromatography (silica gel, 3:1 hexane/EtOAc) provided 4.4 g (69%) of enone 7.

Step 2: Preparation of THF ether (8)

Sodium tetrahydridoborate (194 mg, 5.14 mmol) was added to a stirred solution of enone 7 (2.36 g, 5.14 mmol) in MEOH (10.3 mL) at 0° C. After 2 h the solvent was removed in vacuo and the residue was diluted with saturated aqueous ammonium chloride and EtOAc. The organic portion was separated, washed with brine, dried (MgSO$_4$), filtered and concentrated in vacuo to provide the corresponding allylic alcohol as a viscous oil.

A solution of the allylic alcohol and Wilkinson's catalyst (775 mg, 0.84 mmol) in THF (7.0 mL) was evacuated and purged under an atmosphere of hydrogen gas. After 12 h the solvent was removed in vacuo and the residue was purified by FCC (silica gel, 3:1 hex/EtOAc) to furnish 824 mg (29%) of the corresponding dihydro alcohol.

The dihydro alcohol (prepared above), 3,4-dihydro-2H-pyran (1.4 mL, 15.4 mmol) and and pyridinium p-toluenesulfonate (39 mg, 0.15 mmol) in CH$_2$Cl$_2$ (3.1 mL) was stirred at 23° C. for 12 h. The reaction was diluted with EtOAc and washed with 1N HCl, saturated aq. NaHCO$_3$ and brine. The organic portion was dried (MgSO$_4$), filtered and concentrated in vacuo. The residue was purified by FCC (silica gel, 3:1 hex EtOAc) to afford 727 mg (75%) of THF protected ether 8.

Step 3: Addition of α-chain to 8:

Diisobutylaluminum hydride (0.86 mL of a 1.0 M solution in CH$_2$Cl$_2$, 0.86 mmol) was added to a solution of lactone 8 (313 mg, 0.57 mmol) in CH$_2$Cl$_2$ (1.2 mL) at −78° C. After 0.5 h the reaction was quenched with saturated aqueous sodium potassium tartrate and allowed to warm to room temperature. The mixture was extracted with CH$_2$Cl$_2$ and the organic portion was washed with brine, dried (Na$_2$SO$_4$), filtered then concentrated in vacuo to provide the corresponding lactol as a clear, colorless oil.

To a suspension of (4-carboxybutyl) triphenylphosphonium bromide (800 mg, 1.80 mmol) in THF (7.2 mL) was added potassium bis(trimethylsilyl) amide (718 mg, 3.6 mmol) at 0° C. After 0.5 h the reddish-orange mixture was cooled to −78° C. and a solution of the lactol (prepared above) in THF (3.0 mL) was added. The reaction mixture was allowed to warm to room temperature on its own accord. At this time it was quenched with saturated aqueous NH$_4$Cl and then extracted with EtOAc. The organic portion was washed with brine, dried (MgSO$_4$), filtered and concentrated in vacuo. FCC (silica gel, 3:2 EtOAc/hex) afforded 180.5 mg (50%) of free acid 10.

Step 4: Deprotection of bis-THF protected acid 10:

A solution of 10 (44 mg, 0.07 mmol) and pyridinium p-toluenesulfonate (21 mg, 0.084 mmol) in MEOH (1.0 mL) was stirred at 23° C. for 12 h. The solvent was removed in vacuo. The residue was diluted with EtOAc and then washed with 1N HCl, saturated aqueous NaHCO$_3$, and brine. The organic portion was dried over MgSO$_4$, filtered and concentrated in vacuo. Purification of the residue by flash column chromatography (silica gel, 100% EtOAc) gave 15 mg (46%) of trihydroxy acid 5f.

EXAMPLE 7

7-[3α, 5α-Dihydroxy-2-(3(3α-hydroxy-5-(5-(2-cyano)thienyl)-1E-pentenyl)cyclopentyl]-5Z-heptenamide (11a)

Ammonia gas (~4.5 mL) was condensed at −78° C. into a tube containing trihydroxy ester 4a (52 mg, 0.12 mmol) and ammonium chloride (192 mg, 3.56 mmol). The tube was then sealed and heated to 60° C. for 24 h. At this time the tube was cooled to −78° C., vented and allowed to warm to room temperature on its own accord. The residue was dissolved in saturated aqueous NH$_4$Cl and EtOAc. The organic portion was separated, dried over anhydrous MgSO$_4$, filtered and the filtrate was concentrated in vacuo. The residue was purified by flash column chromatography (silica gel, 9:1 CH$_2$Cl$_2$/MeOH) to provide 15 mg (30%) of the title compound 11a.

EXAMPLE 8

7-[3α, 5α-Dihydroxy-2-(3α-hydroxy-5-(5-(2,3,4-trichloro)thienyl)-1E-pentenyl)cyclopentyl]-5Z-heptenamide (11b)

In accordance with the procedures described above for the synthesis of 11a, the use of trihydroxy ester 4b afforded 22 mg of amide 11b.

EXAMPLE 9

7-[3α, 5α-Dihydroxy-2-(3α-hydroxy-5-(5-(2,3-dichloro)thienyl)-1E-pentenyl)cyclopentyl]-5Z-heptenamide (11c)

In accordance with the procedures described above for the synthesis of 11a, *the use of trihydroxy ester* 4c afforded 6 mg of amide

EXAMPLE 10

7-[3α, 5α-Dihydroxy-2-(3α-hydroxy-5-(5-(2-iodo-4-methyl)thienyl)-1E-pentenyl)cyclopentyl]-5-heptenamide (11d)

In accordance with the procedures described above for the synthesis of 11a, the use of trihydroxy ester 4d afforded 6 mg of amide 11d.

EXAMPLE 11

7-[3α, 5α-Dihydroxy-2-(3α-hydroxy-5-5-(3-(2,5-dichloro)thienyl)-pentenyl)cyclopentyl]-5Z-heptenamide (11f)

A solution of free acid 10 (78 mg, 0.123 mmol), iodomethane (77 mL, 1.23 mmol) and 1,8-diazabicyclo [5.4.0]undec-7-ene (0.11 mL, 0.74 mmol) in acetone (1.0 mL) was stirred at 23° C. for 12 h. The reaction mixture was concentrated in vacuo and the residue was purified by flash column chromatography (silica gel, 3:1 EtOAc/hexane) to yield 53 mg of the corresponding methyl ester.

A solution of the methyl ester (53 mg, 0.082 mmol) and pyridinium p-toluenesulfonate (25 mg, 0.098 mmol) in MeOH (0.5 mL) was stirred at 23° C. for 12 h. The solvent was removed in vacuo. The residue was diluted with EtOAc and then washed with 1N HCl, saturated aqueous NaHCO$_3$, and brine. The organic portion was dried over MgSO$_4$, filtered and concentrated in vacuo. Purification of the residue by flash chromatography (silica gel, 100% EtOAc) gave 28 mg of the corresponding trthydroxy ester.

Ammonia gas (~4.0 mL) was condensed at ~78° C. into a tube containing the trthydroxy ester (52 mg, 0.12 mmol) prepared above and ammonium chloride (122 mg, 2.28 mmol). The tube was then sealed and heated to 60° C. for 72 h. At this time the tube was cooled to −78° C, vented and allowed to warm to room temperature on its own accord. The residue was dissolved in saturated aqueous NH$_4$Cl and EtOAc. The organic portion was separated, dried over anhydrous MgSO$_4$, filtered and the filtrate was concentrated in vacuo. The residue was purified by flash column chromatography (silica gel, 9:1 CH$_2$Cl$_2$/MeOH) to provide 17 mg (52%) of the title compound 11f.

EXAMPLE 12

N-2-Hydroxyethyl 7-[3α, 5α-dihydroxy-2-(3α-hydroxy-5-(5-(3-bromo-2-methyl)thienyl)-1E-pentenyl)cyclopentyl]-5Z-heptenamide (11g)

A solution of trihydroxy ester 4g (36 mg, 0.742 mmol) and 2-hydroxyethylamine (0.43 mL, 7.2 mmol) in MeOH (4.0 mL) was heated to 80° C. for 48 h. The reaction was cooled to room temperature and concentrated in vacuo. The residue was purified by FCC (silica gel, 9:1 CH$_2$Cl$_2$/MeOH) to afford 35 mg (92%) of amide 11g.

EXAMPLE 13

N-Ethyl 7-[3α, 5α-dihydroxy-2-(3α-hydroxy-5-(5-(3-bromo-2-methyl)thienyl)-1E-pentenyl)cyclopentyl]-5Z-heptenamide (11h)

In accordance with the procedures described above for the synthesis of 11g, the use of ethylamine afforded 25 mg (66%) of amide 11h.

EXAMPLE 14

N-2-Hydroxyethyl 7-3α, 5α-dihydroxy-2-(3α-hydroxy-5-(3-(2,5-dibromo)-thienyl)-1E-pentenyl)cyclopentyl]-5Z-heptenamide (11i)

In accordance with the procedures described above for the synthesis of 11g, the use of trihydroxy ester 4i afforded 30 mg (58%) of amide 11i.

EXAMPLE 15

N-Ethyl 7-[3α, 5α-dihydroxy-2-(3α-hydroxy-5-(3-(2,5-dibromo)-thienyl)-1E-pentenyl)cyclopentyl]-5Z-heptenamide (11j)

In accordance with the procedures described above for the synthesis of 11h, the use of trihydroxy ester 4j afforded 30 mg (61%) of amide 11j.

EXAMPLE 16

Isopropyl 7-[3α, 5α-Dihydroxy-2-(3α-hydroxy-5-(5-(2-cyano)thienyl)-1E-pentenyl)cyclopentyl]-5Z-heptenoate (12a)

A solution of free acid 5a (38 mg, 0.090 mmol), 2-iodopropane (45 mL, 0.45 mmol) and 1,8-diazabicyclo[5.4.0]undec-7-ene (40 mL, 0.27 mmol) in acetone (0.18 mL) was stirred at 23° C. for 12 h. The reaction mixture was concentrated in vacuo and the residue was purified by flash column chromatography (silica gel, 3:1 EtOAc/hexane) to yield 15 mg (36%) of the isopropyl ester 12a.

EXAMPLE 17

Isopropyl 7-[3α, 5α-Dihydroxy-2-(3α-hydroxy-(5-(2,3,4-trichloro)-thienyl)-1E-pentenyl)cyclopentyl]-5Z-heptenoate (12b)

In accordance with the procedures described above for the synthesis of 12a, the use of free acid 5b afforded 12 mg (50%) of amide 12b.

EXAMPLE 18

Isopropyl 7-[3α, 5α-Dihydroxy-2-(3α-hydroxy-5-(5 (3-bromo-2-methyl)-thienyl)-1E-pentenyl) cyclopentyl]-5Z-heptenoate (12k)

In accordance with the procedures described above for the synthesis of 12a, the use of free acid 5k afforded 24 mg (56%) of amide 12k.

EXAMPLE 19

Isopropyl 7-[3α, 5α-Dihydroxy-2-(3α-hydroxy-5-(3-(2,dibromo)-thienyl)-1E-pentenyl)cyclopentyl]-5Z-heptenoate (12l)

In accordance with the procedures described above for the synthesis of 12a, the use of free acid 5l afforded 10 mg (14%) of amide 12l.

Certain of the above compounds were tested for activity in the various in vitro assays described below and the results are reported in the Table.

Activity at different prostanoid receptors was measured in vitro in isolated smooth muscle preparations. FP-activity was measured as contraction of the isolated feline iris sphincter. EP$_1$-activity was measured as contraction of the longitudinal smooth muscle of the isolated guinea pig ileum. EP$_3$-activity was measured as inhibition of the twitch response induced by electrical field stimulation in the isolated guinea pig was deferens and as contraction of the longitudinal smooth muscle of the isolated chick ileum. Activity was also measured as relaxation of smooth muscle of isolated rabbit jugular vein a preparation which appears to contain a unique PGF$_{2\alpha}$-sensitive receptor provisionally termed FP$_{VASC}$. TP-vasoconstrictor activity was measured as contraction of rings of the isolated rat thoracic aorta. Effects on platelets from healthy human donors were measured by incubating platelet-rich plasma with the compounds described herein. inhibition of aggregation was determined by the ability of the compounds described herein to inhibit platelet aggregation in platelet-rich plasma induced by 20 µM ADP.

In addition to stimulating the FP receptor associated with the cat iris, several examples also stimulated the EP$_3$ receptor. Compounds with agonist activity at EP$_3$ receptors may also be used for treating gastric or duodenal ulcer by virtue of their cytoprotective and anti-secretory properties. They may also be used as adjunctive therapy in combination with aspirin-like drugs and steroids to limit gastrointestinal side effects. EP$_3$ agonists stimulate uterine smooth muscle and may be used to terminate pregnancy in human females. EP$_3$ agonists are also useful in the cervical ripening process and could be used for inducing labor.

| AGN-# | FP | EP$_1$ | EP$_3$ | DP/EP$_2$ | EP$_4$ | FP/EP$_4$ Ratio | TP | Platelets aggreg inhib | Dog IOP (1 day) | Monkey IOP (5 day) | Hyp/Mi-osis |
|---|---|---|---|---|---|---|---|---|---|---|---|
| 194210 4ab | 28 | NA | | | 120 | 0.23 | >10$^4$ | | | | |
| 194257 16f | 1620 | | | | 5438 | 0.3 | | | | | |
| 194262 8w | 26 | | | | 150600 | 0.0002 | | | | | |
| 194263 4ac | 3 | >10$^4$ | | | 64 | 0.05 | 7940 | | | | |
| 194329 8x | 214 | | | | | | | | | | |
| 194330 16g | 40 | | | | | | | | | | |
| 194338 4ad | 24 | | | | | | | | | | |

-continued

| AGN-# | FP | EC$_{50}$ (nM) EP$_1$ | EP$_3$ | DP/EP$_2$ | IC$_{25}$ EP$_4$ | FP/EP$_4$ Ratio | TP | Platelets aggreg | inhib | Dog IOP (1 day) | Monkey IOP (5 day) | Hyp/Mi-osis |
|---|---|---|---|---|---|---|---|---|---|---|---|---|
| 194339 17 | 63 | | | | | | | | | | | |

| AGN-# | FP | EC$_{50}$ (nM) EP$_1$ | EP$_3$ | DP/EP$_2$ | IC$_{25}$ EP$_4$ | FP/EP$_4$ Ratio | TP | Platelets aggreg | inhib | Dog IOP (1 day) | Monkey IOP (5 day) | Hyp/Mi-osis |
|---|---|---|---|---|---|---|---|---|---|---|---|---|
| 5a | 43 | | | | | | | | | | | |
| 5b | 12 | | | | | | | | | | | |
| 5c | 0.7 | | | | | | | | | | | |
| 5d | | | | | | | | | | | | |
| 5e | 3800 | | | | 11775 | 03 | | | | | | |
| 5f | 20 | >>10$^4$ | | | | | | 6920 | | | | |
| | 2950 | | | | | | | | | | | |

-continued

| | | EC$_{50}$ (nM) | | | IC$_{25}$ | FP/EP$_4$ | | Platelets | | Dog IOP | Monkey IOP | Hyp/Mi- |
|---|---|---|---|---|---|---|---|---|---|---|---|---|
| AGN-# | FP | EP$_1$ | EP$_3$ | DP/EP$_2$ | EP$_4$ | Ratio | TP | aggreg | inhib | (1 day) | (5 day) | osis |
| 11a | | | | | | | | | | | | |
| 11b | 35 | | | | | | | | | | | |
| 11c | | | | | | | | | | | | |

| | | EC$_{50}$ (nM) | | | IC$_{25}$ | FP/EP$_4$ | | Platelets | | Dog IOP | Monkey IOP | Hyp/Mi- |
|---|---|---|---|---|---|---|---|---|---|---|---|---|
| AGN-# | FP | EP$_1$ | EP$_3$ | DP/EP$_2$ | EP$_4$ | Ratio | TP | aggreg | inhib | (1 day) | (5 day) | osis |
| 11d | | | | | | | | | | | | |
| 11f | 8 | NA | | | | | NA | | | | | |
| 11g | 38 | NA | NA | | | | | | | | | |
| 11h | 25 | >>10$^4$ | | | >135,135 | <0.0002 | NA | | | | | |
| 11i | 48 | NA | | | 185,185 | 0.0003 | NA | | | | | |

-continued
| AGN-# | EC$_{50}$ (nM) | | | | IC$_{25}$ | FP/EP$_4$ | | Platelets | | Dog IOP | Monkey IOP | Hyp/ |
| --- | --- | --- | --- | --- | --- | --- | --- | --- | --- | --- | --- | --- |
| | FP | EP$_1$ | EP$_3$ | DP/EP$_2$ | EP$_4$ | Ratio | TP | aggreg | inhib | (1 day) | (5 day) | osis |
| 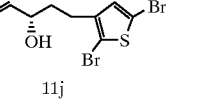 11j | 32 | NA | | | 82360 | 0.0004 | NA | | | | | |
| 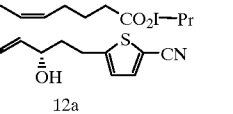 12a | 115 | | | | | | | | | | | |
| 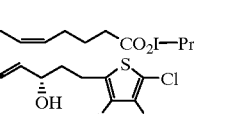 12b | 63 | | | | | | | | | | | |
| 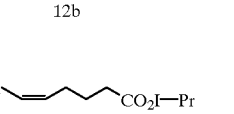 12k | 10 | NA | NA | | | | | | | | | |
| 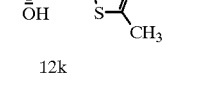 12l | 79 | | | | | | NA | | | | | |
| AGN-# | EC$_{50}$ (nM) | | | | IC$_{25}$ | FP/EP$_4$ | | Platelets | | Dog IOP | Monkey IOP | Hyp/ |
| --- | --- | --- | --- | --- | --- | --- | --- | --- | --- | --- | --- | --- |
| | FP | EP$_1$ | EP$_3$ | DP/EP$_2$ | EP$_4$ | Ratio | TP | aggreg | inhib | (1 day) | (5 day) | osis |
| 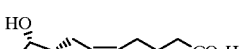 194013 4x | 18 | >>10$^4$ | | | 57 | 0.3 | | | | | | |
| 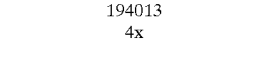 194042 16a | 7.1 | | | | 29685 | 0.0002 | >10$^4$ | NA | NA | | | |

-continued
| AGN-# | EC₅₀ (nM) FP | EP₁ | EP₃ | DP/EP₂ | IC₂₅ EP₄ | FP/EP₄ Ratio | TP | Platelets aggreg | inhib | Dog IOP (1 day) | Monkey IOP (5 day) | Hyp/ Miosis |
|---|---|---|---|---|---|---|---|---|---|---|---|---|
| 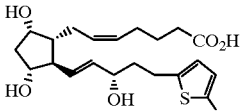 194043 4y | 1.8 | >10⁴pa | | | 335 | 0.005 | 2510 | | | 0.1%/ −5.5 | | |
| 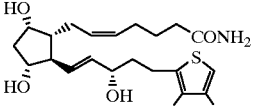 194045 8r | 53 | | | | 28090 | 0.002 | | | | | | |
| 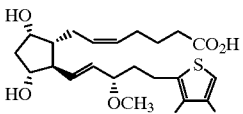 194047 16b | 60 | | | | 824 | 0.07 | | | | | | |
| 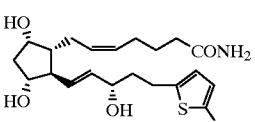 194054 8s | 8.6 | NA | | | 46200 | 0.0002 | >10⁴ | NA | >>10⁴ | 0.01%/ −3.4 0.1%/ −3.0 | | |
| 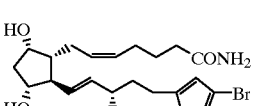 194079 8t | 5.6 | >>10⁴ | | | 26393 | 0.0002 | >10⁴ | NA | NA | 0.1%/ −4.2 | | |
| AGN-# | EC₅₀ (nM) FP | EP₁ | EP₃ | DP/EP₂ | IC₂₅ EP₄ | FP/EP₄ Ratio | TP | Platelets aggreg | inhib | Dog IOP (1 day) | Monkey IOP (5 day) | Hyp/ Miosis |
|---|---|---|---|---|---|---|---|---|---|---|---|---|
| 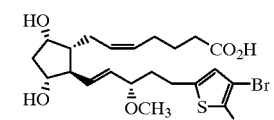 194080 | 5.9 | NA | | | 133 | 0.04 | NA | | | | | |

-continued

| AGN-# | EC$_{50}$ (nM) | | | | IC$_{25}$ | FP/EP$_4$ | Platelets | | Dog IOP | Monkey IOP | Hyp/ |
| --- | --- | --- | --- | --- | --- | --- | --- | --- | --- | --- | --- |
| | FP | EP$_1$ | EP$_3$ | DP/EP$_2$ | EP$_4$ | Ratio | TP aggreg | inhib | (1 day) | (5 day) | Mi-osis |
| 194081 16c | 0.9 | NA | | | 25 | 0.04 | 4570 | | | | |
| 194179 4z | 92 | | | | 1070 | 0.09 | | | | | |
| 194198 16d | 12 | NA | | | 186490 | 0.00006 | NA | NA | NA | 0.01%/ −0.7 0.1%/ −4.4 | |
| 194199 8u | 5.9 | | | | 16 | 0.4 | | | | | |
| 194208 4aa | 288 | | | | 1130 | 0.25 | | | | | |
| 194209 16e | 234 | | | | 106655 | 0.02 | | | | | |
| 8v | | | | | | | | | | | |

Other potential therapeutic applications are in osteoporosis, constipation, renal disorders, sexual dysfunction, baldness, diabetes, cancer and in disorder of immune regulation.

Many examples also have pronounced activity at the FP receptor, provisionally termed FP$_{VASC}$ associated with the vascular endothelium in the rabbit jugular vein preparation. Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension.

The compounds of the invention may also be useful in the treatment of various pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petroatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules made of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rich starchy, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injectionsuspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

I claim:

1. A method of treating ocular hypertension which comprises administering to a mammal having ocular hypertension a therapeutically effective amount of a cyclopentane heptan(ene)oic acid, 2-heteroaryl alkenyl compound represented by formula II

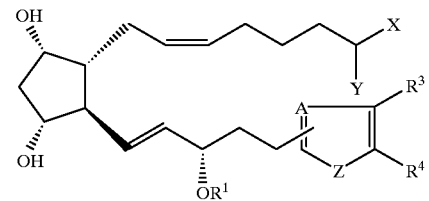

wherein the hatched segments represent α bonds, the solid triangle represents a β bond, the wavy line represents either an α or β bond, $R^1$ is hydrogen or a lower alkyl radical hazing up to six carbon atoms, X is selected from the soup consisting of —$OR^1$ and —$N(R^1)_2$; Y is =O or represents 2 hydrogen radicals, Z is selected from the group consisting of O and S, A is C when A is bonded directly to said alkenyl of said 2-heteroalkenyl of the compound and $CR^2$ when A is not bonded directly to said alkenyl of said 2-heteroalkenyl of the compound, $R^2$, $R^3$ and $R^4$ are selected from the group consisting of hydrogen, halogen, cyano and lower alkyl having from 1 to 6 carbon atoms and the 9,11, or 15 alkyl esters thereof.

2. The method of claim 1 wherein said compound represented by formula III:

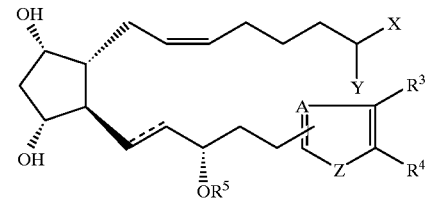

wherein $R^5$ is hydrogen.

3. The method of claim 2 wherein X is —OH or —$NH_2$.

4. The method of claim 2 wherein Y is =O and X is —OH.

5. The method of claim 2 wherein Y is =O and X is —$NH_2$.

6. The method of claim 2 wherein Z is S.

7. The method of claim 6 wherein at least one of $R^2$, $R^3$ and $R^4$ are selected from the group consisting of cyano, chloro, bromo, iodo and methyl.

8. The method of claim 6 wherein at least one of $R^2$, $R^3$ and $R^4$ is cyano.

9. The method of claim 6 wherein at least two of $R^2$, $R^3$ and $R^4$ are chloro.

10. The method of claim 6 wherein at least two of $R^2$, $R^3$ and $R^4$ are bromo.

11. The method of claim 6 wherein at least two of $R^2$, $R^3$ and $R^4$ are methyl.

12. The method of claim 6 wherein at least one of $R^2$, $R^3$ and $R^4$ is methyl and at least one of $R^2$, $R^3$ and $R^4$ are chloro.

13. The method of claim 11 wherein at least one of $R^2$, $R^3$ or $R^4$ are bromo and at least one of $R^2$, $R^3$ or $R^4$ are methyl.

14. The method of claim 13 wherein said compound is selected from the group consisting of 7-[3α, 5α-Dihydroxy-2-(3α-hydroxy-5-(5-(2-cyano)thienyl)-1E-pentenyl)cyclopentyl]-5Z-heptenoic acid (5a)

7-[3α, 5α-Dihydroxy-2-(3α-hydroxy-5-5-(5-(2,3,4-trichloro)thienyl)-1E-pentenyl)cyclopentyl]-5Z-heptenoic acid (5b)

b 7-[3α, 5α-Dihydroxy-2-(3α-hydroxy-5-(5-(2,3-dichloro)thienyl)-1E-pentenyl)cyclopentyl]-5Z-heptenoic acid (5c)

7-[3α, 5-Dihydroxy-2-(3α-hydroxy-5(-5-(2-iodo-4-methyl)thienyl)-1E-pentenyl)cyclopentyl]-5Z-heptenoic acid (5d)

b 7-[3α, 5α-Dihydroxy-2-(3α-hydroxy-5-(3-bromo-2,5-dimethyl)thienyl)-1E-pentenyl)cyclopentyl]-5Z-heptenoic acid (5e)

7-[3α, 5α-Dihydroxy-2-(3α-hydroxy-5-(3-(2,5-dichloro)thienyl)pentyl)-cyclopentyl]-5Z-heptenoic acid (5f)

7-[3α, 5α-Dihydroxy-2-(3α-hydroxy-5-(5-(2-cyano)thienyl)-1E-pentenyl)cyclopentyl]-5Z-heptenamide (11a)

7-[3α, 5α-Dihydroxy-2-(3α-hydroxy-5-(5-(2,3,4-trichloro)thienyl)-1E-pentenyl)cyclopentyl]-5Z-heptenamide (11b)

7-[3α, 5α-Dihydroxy-2-(3α-hydroxy-5-(5-(2,3-dichloro)thienyl)-1E-pentenyl)cyclopentyl]-5Z-heptenamide (11c)

7-[3α, 5α-Dihydroxy-2-(3α-hydroxy-5-(5-(2-iodo-4-methyl)thienyl)-1E-pentenyl)cyclopentyl]-5Z-heptenamnide (11d)

7-[3α, 5α-Dihydroxy-2-(3α-hydroxy-5-(3-(2,5-dichloro)thienyl)-pentyl)cyclopentyl]-5Z-heptenamide (11f)

N-2-Hydroxyethyl 7-[3α, 5α-dihydroxy-2-(3α-hydroxy-5-(5-(3-bromo-2-methyl)thienyl)-1E-pentenyl)cyclopentyl]-5Z-heptenamide (11g)

N-Ethyl 7-[3α, 5α-dihydroxy-2-(3α-hydroxy-5-(5-(3-bromo-2-methyl)thienyl)-1E-pentenyl)cyclopentyl]-5Z-heptenamide (11h)

N-2-Hydroxyethyl 7-[3α, 5α-dihydroxy-2-(3α-hydroxy-5-(3-(2,5-dibromo)-thienyl)-1E-pentenyl)cyclopentyl]-5Z-heptenamide (11i)

N-Ethyl 7-[3α, 5α-dihydroxy-2-(3α-hydroxy-5-(3-(2,5dibromo)-thienyl)-1E-pentenyl)cyclopentyl]-5Z-heptenamide (11j)

Isopropyl 7-[3α, 5α-Dihydroxy-2-(3α-hydroxy-5-(5-(2-cyano)thienyl)-1E-pentenyl)cyclopentyl]-5Z-heptenoate (12a)

Isopropyl 7-[3α, 5α-Dihydroxy-2-(3α-hydroxy-5-(5-(2,3,4-trichloro)-thienyl)-1E-pentenyl)cyclopentyl]-5Z-heptenoate (12b)

Isopropyl 7-[3α, 5α-Dihydroxy-2-(3α-hydroxy-5-(5-(3-bromo-2-methyl)-thienyl)-1E-pentenyl)cyclopentyl]-5Z-heptenoate (12k) and Isopropyl 7-[3α, 5α-Dihydroxy-2-(3α-hydroxy-5-(3-(2,5dibromo)-thienyl)-1E-pentenyl)cyclopentyl]-5Z-heptenoate (12l).

15. The cyclopentane heptan(ene)oic acid, 2-heteroarylalkenyl compound represented by Formula III:

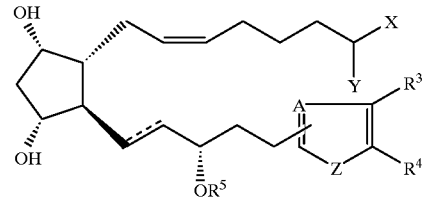

wherein the hatched segments represent α bonds, the solid triangle represents a β bond; the dashed bond represents a double bond or a single bond; $R^5$ represents hydrogen or a lower alkyl radical having up to six carbon atoms; X is selected from the group consisting of $-OR^1$ and $-N(R^1)_2$; Y is $=O$ or represents 2 hydrogen radicals; $R^1$ is hydrogen or a lower alkyl radical having up to six carbon atoms; Z is selected from the group consisting of O and S, A is C when A is bonded directly to said alkenyl of said 2-heteroalkenyl of the and $CR^2$ when A is not bonded directly to said alkenyl of said 2-hetero alkenyl of the compound; $R^2$, $R^3$ and $R^4$ are selected from the group consisting of hydrogen, halogen, cyano and lower alkyl having from 1 to 6 carbon atoms; wherein at least two of the radicals represented by $R^2$, $R^3$ and $R^4$ are halogen, cyano, or a lower alkyl radical having from 1 to 6 carbon atoms; and the 9,11, or 15 alkyl esters thereof.

16. The cyclopentane heptan(ene)oic acid, 2-heteroarylalkenyl compound represented by Formula III:

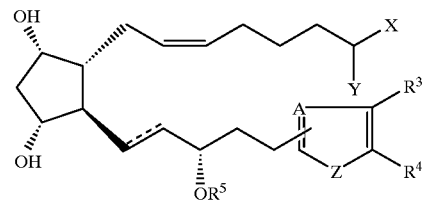

wherein the hatched segments represent α bonds, the solid triangle represents a β bond; the dashed bond represents a double bond or a single bond; $R^5$ represents hydrogen or a lower alkyl radical having up to six carbon atoms, X is selected from the group consisting of $-OR^1$ and $-N(R^1)_2$; Y is $=O$ or represents 2 hydrogen radicals; $R^1$ is hydrogen or a lower alkyl radical having up to six carbon atoms; Z is S, A is C when A is bonded directly to said alkenyl of said 2-heteroalkenyl of the and $CR^2$ when A is not bonded directly to said alkenyl of said 2-hetero alkenyl of the compound; $R^2$, $R^3$ and $R^4$ are selected from the group consisting of hydrogen, halogen, cyano and lower allyl having from 1 to 6 carbon atoms; wherein at least two of the radicals represented by $R^2$, $R^3$ and $R^4$ are halogen, cyano, or a lower 1 radical having from 1 to 6 carbon atoms; and the 9, 11, or 15 alkyl esters thereof.

17. The compound of claim 16 wherein at least one of $R^2$, $R^3$ and $R^4$, are selected from the group consisting of cyano, chloro, bromo, iodo and methyl.

18. The compound of claim 17 wherein at least one of $R^2$, $R^3$ and $R^4$ is cyano.

19. The compound of claim 17 wherein at least two of $R^2$, $R^3$ and $R^4$ are chloro.

20. The compound of claim 17 wherein at least two of $R^2$, $R^3$ and $R^4$ are bromo.

21. The compound of claim 17 wherein at least two of $R^2$, $R^3$ and $R^4$ are methyl.

22. The compound of claim 17 wherein at least one of $R^2$, $R^3$ and $R^4$ is methyl and at least one of $R^2$, $R^3$ and $R^4$ are chloro.

23. The compound of claim 17 wherein at least one of $R^2$, $R^3$ or $R^4$ are bromo and at least one of $R^2$, $R^3$ or $R^4$ are methyl.

24. The compound of claim 17 wherein said compound is selected from the group consisting of 7-[3α, 5α-Dihydroxy-2-(3α-hydroxy-5-(5-(2-cyano) thienyl)-1E-pentenyl)cyclopentyl]-5Z-heptenoic acid (5a)

7-[3α, 5α-Dihydroxy-2-(3α-hydroxy-(5-(2,3,4-trichloro) thienyl)-1E-pentenyl)cyclopentyl]-5Z-heptenoic acid (5b)

7-[3α, 5α-Dihydroxy-2-(3α-hydroxy-5-(5-(2,3-dichloro) thienyl)-1E-pentenyl)cyclopentyl]-5Z-heptenoic acid (5c)

7-[3α, 5α-Dihydroxy-2-(3α-hydroxy-5-(5-(2-iodo-4-methyl)thienyl)-1E-pentenyl)cyclopentyl]-5Z-heptenoic acid (5d)

7-[3α, 5α-Dihydroxy-2-(3α-hydroxy-5-(4-(3-bromo-2,5-dimethyl)thienyl)-1E-pentenyl)cyclopentyl]-5Z-heptenoic acid (5e)

7-[3α, 5α-Dihydroxy-2-(3α-hydroxy-5-(3-(2,5-dichloro) thienyl)pentyl)-cyclopentyl]-5Z-heptenoic acid (5f)

7-[3α, 5α-Dihydroxy-2-(3α-hydroxy-5-(5-(2-cyano) thienyl)-1E-pentenyl)cyclopentyl]-5Z-heptenamide (11a)

7-[3α, 5α-Dihydroxy-2-(3α-hydroxy-5-(5-(2,3,4-trichloro)thienyl)-1E-pentenyl)cyclopentyl]-5Z-heptenamide (11b)

7-[3α, 5α-Dihydroxy-2-(3α-hydroxy-5-(5-(2,5-dichloro) thienyl)-1E-pentenyl)cyclopentyl]-5Z-heptenamide (11c)

7-[3α, 5α-Dihydroxy-2-(3α-hydroxy-5-(5-(2-iodo-4-methyl)thienyl)-1E-pentenyl)cyclopentyl]-5Z-heptenamide (11d)

7-[3α, 5α-Dihydroxy-2-(3α-hydroxy-5-(3-(2,5-dichloro) thienyl)-pentyl)cyclopentyl]-5Z-heptenamide (11f)

N-2-Hydroxyethyl 7-[3α, 5α-dihydroxy-2-(3α-hydroxy-5-(5-(3-bromo-2-methyl)thienyl)-1E-pentenyl) cyclopentyl]-5Z-heptenamide (11g)

N-Ethyl 7-[3α, 5α-dihydroxy-2-(3α-hydroxy-5-(5-(3-bromo-2-methyl)thienyl)-1E-pentenyl)cyclopentyl]-5Z-heptenamnide (11h)

N-2-Hydroxyethyl 7-[3α, 5α-dihydroxy-2-(3α-hydroxy-5-(3-(2,5-dibromo)-thienyl)-1E-pentenyl)cyclopentyl]-5Z-heptenamnide (11i)

N-2-Hydroxyethyl 7-[3α, 5α-dihydroxy-2-(3α-hydroxy-5-(3-(2,5-dibromo)-thienyl)-1E-pentenyl)cyclopentyl]-5Z-heptenamnide (11i)

N-Ethyl 7-[3α, 5α-dihydroxy-2-(3α-hydroxy-5-(3-(2,5-dibromo)-thienyl)-1E-pentenyl)cyclopentyl]-5Z-heptenamnide (11j)

Isopropyl 7-[3α, 5α- Dihydroxy-(2-(3α-hydroxy-5-(2-cyano)thienyl)-1E-pentenyl)cyclopentyl]-5Z-heptenoate (12a)

Isopropyl 7-[3α, 5α- Dihydroxy-(2-(3α-hydroxy-5-(5-(2,3,4-thienyl)-1E-pentenyl)cyclopentyl]-5Z- heptenoate (12b)

Isopropyl 7-[3α, 5α-Dihydroxy-2-(3α-hydroxy-5-(5-(3-bromo)2-methyl)-thienyl)-1E-pentenyl)cyclopentyl]-5Z-heptenoate (12k)

Isopropyl 7-[3α, 5α-Dihydroxy-2-(3α-hydroxy-5-(3-(2,5-dibromo)-thienyl)-1E-pentenyl)cyclopentyl]-5Z-heptenoate (12l).

* * * * *

UNITED STATES PATENT AND TRADEMARK OFFICE
CERTIFICATE OF CORRECTION

PATENT NO. : 6,124,344            Page 1 of 2

DATED : September 26, 2000

INVENTOR(S) : Burk

It is certified that error appears in the above-identified patent and that said Letters Patent is hereby corrected as shown below:

```
Column 1, line 49; after "Schlemm" insert --.--
Column 2, line 26; delete second occurrence of "α" and insert in place
 thereof --β--
Column 2, line 26; delete "erg" and insert in place thereof --e.g.--
Column 2, line 67; delete "1-acyl" and insert in place thereof --11-acyl--
Column 3, line 1; delete "1-acetyl, 1-isobutyryl, 1-valeryl" and insert
 in place thereof --11-acetyl, 11-isobutyryl, 11-valeryl--
Column 3, line 59; delete "SO₂NH₂1" and insert in place thereof --SO₂NH₂:--
Column 4, line 43; delete "a" and insert in place thereof --α--
Column 4, line 67; delete "5"
Column 5, line 30; delete "(2-iodomethyl)" and insert in place thereof
 --(2-iodo-4-methyl)--
Column 5, line 33; delete "5-((3-bromo-" and insert in place thereof
 --5-4-(3-bromo- --
Column 5, line 40; delete "(2,3,-" and insert in place thereof --(2,3,4- --
Column 5, line 42; delete "5(-5-" and insert in place thereof --5-(5- --
Column 6, line 6; delete "(1211)" and insert in place thereof --(121)--
Column 7, line 64; delete "(4b/)" and insert in place thereof --(4b)--
Column 8, line 41; delete "-(5-(2-" and insert in place thereof --5-(5-2- --
Column 9, line 35; delete "THF" and insert in place thereof --THP--
Column 9, line 61; delete "THF" and insert in place thereof --THP--
Column 10, line 8; delete "2-(3(3α-" and insert in place thereof --2-(3α- --
Column 10, line 41; after "amide" insert --(11c)--
Column 10, line 46; delete "5" and insert in place thereof --5Z--
Column 10, line 54; delete "5-5-" and insert in place thereof --5-(5- --
Column 11, line 6; delete "trthdroxy" and insert in place thereof --trihydroxy--
Column 11, line 8; delete "trthdroxy" and insert in place thereof --trihydroxy--
Column 11, line 43; delete "7-3α" and insert in place thereof --7-[3α--
Column 12, line 8; delete "-(5-" and insert in place thereof --5-(5- --
Column 12, line 28; delete "(3-(2,-" and insert in place thereof --(3-(2,5- --
Column 16, formula 5e under heading FP/EP4 Ratio; delete "03" and insert in
 place thereof --0.3--
```

UNITED STATES PATENT AND TRADEMARK OFFICE
CERTIFICATE OF CORRECTION

PATENT NO. : 6,124,344

DATED : September 26, 2000

INVENTOR(S) : Burk

It is certified that error appears in the above-identified patent and that said Letters Patent is hereby corrected as shown below:

Column 25, line 66; delete "injectionsuspension" and insert in place thereof --injection suspension--

IN THE CLAIMS:
Column 26, line 36; delete "hazing" and insert in place thereof --having--
Column 26, line 36; delete "soup" and insert in place thereof --group--
Column 27, line 21; delete "b"
Column 27, line 27; delete "b"
Column 27, line 27; delete "5-(3-" and insert in place thereof --5-(4-(3-- --
Column 27, line 57; delete "5dibromo" and insert in place thereof --5-dibromo--
Column 28, line 2; delete "5dibromo" and insert in place thereof --5-dibromo--
Column 28, line 25; after "the" insert --compound--
Column 28, line 56; delete "allyl" and insert in place thereof --alkyl--
Column 29, line 16; delete "(5-(2,3,4" and insert in place thereof --5-(5-(2,3,4- --
Column 29, line 37; delete "2,5" and insert in place thereof --2,3--
Column 30, line 24; delete "5-(2-" and insert in place thereof --5-(5-(2-- --
Column 30, line 32; delete "bromo)2" and insert in place thereof --bromo-2--

Signed and Sealed this

Fifteenth Day of May, 2001

*Attest:*

NICHOLAS P. GODICI

*Attesting Officer*    *Acting Director of the United States Patent and Trademark Office*